(12) United States Patent
Schulz

(10) Patent No.: US 11,369,360 B2
(45) Date of Patent: Jun. 28, 2022

(54) ORTHOPAEDIC BONE ANCHOR AND SUSPENSION DEVICE

(71) Applicant: Christoph Schulz, Munich (DE)

(72) Inventor: Christoph Schulz, Munich (DE)

(*) Notice: Subject to any disclaimer, the term of this patent is extended or adjusted under 35 U.S.C. 154(b) by 154 days.

(21) Appl. No.: 16/329,353

(22) PCT Filed: Sep. 11, 2017

(86) PCT No.: PCT/EP2017/072722
§ 371 (c)(1),
(2) Date: Feb. 28, 2019

(87) PCT Pub. No.: WO2018/050589
PCT Pub. Date: Mar. 22, 2018

(65) Prior Publication Data
US 2019/0216456 A1    Jul. 18, 2019

(30) Foreign Application Priority Data
Sep. 16, 2016 (DE) .................... 10 2016 117 490.4

(51) Int. Cl.
*A61B 17/04* (2006.01)
*A61B 17/68* (2006.01)
*A61B 17/84* (2006.01)

(52) U.S. Cl.
CPC .......... *A61B 17/0401* (2013.01); *A61B 17/68* (2013.01); *A61B 17/686* (2013.01);
(Continued)

(58) Field of Classification Search
CPC .... A61B 2017/0403; A61B 2017/0412; A61B 2017/0414; A61B 2017/0427;
(Continued)

(56) References Cited

U.S. PATENT DOCUMENTS 4,590,928 A * 5/1986 Hunt ............... A61B 17/686
606/327
5,354,298 A  10/1994 Lee et al.
(Continued)

FOREIGN PATENT DOCUMENTS

DE   694 00 714 T2   3/1997
EP   0 611 551       10/1996
(Continued)

OTHER PUBLICATIONS

International Search Report dated Nov. 13, 2017 in PCT/EP2017/072722.
Written Opinion dated Nov. 13, 2017 in PCT/EP2017/072722.

*Primary Examiner* — Katherine H Schwiker
(74) *Attorney, Agent, or Firm* — Grüneberg and Myers PLLC

(57) ABSTRACT

An orthopaedic bone anchor and suspension device includes a head which, on its upper face, has an opening of a central bore for receiving an expansion device, and, adjoining the underside of the head, a sleeve which is designed as an expansion dowel for anchoring the bone anchor and suspension device in the bone. The bone anchor and suspension device is characterized in that the head has a collar which protrudes outwards past the sleeve, wherein the collar preferably has holes for the attachment of fastening sutures and, on its outer circumference, has at least one recess for grafts.

20 Claims, 4 Drawing Sheets

(52) U.S. Cl.
CPC ..... *A61B 17/844* (2013.01); *A61B 2017/0403* (2013.01); *A61B 2017/044* (2013.01); *A61B 2017/0409* (2013.01); *A61B 2017/0414* (2013.01); *A61B 2017/0427* (2013.01); *A61B 2017/0438* (2013.01)

(58) Field of Classification Search
CPC ...... A61B 2017/0438; A61B 2017/044; A61B 2017/042–0425; A61B 17/686; A61B 17/844; A61B 17/68; A61B 17/683; A61B 17/685; A61B 17/846; A61B 17/848; A61B 17/8605–862; A61B 17/0401; A61B 2017/0406; A61B 2017/0408; A61B 2017/0429–0437; A61B 2017/0445; A61B 2017/0446–0462; A61B 2017/0464; A61F 2002/0858; A61F 2002/0864; A61F 2002/0841; A61F 2002/0888; A61F 2/0811; A61F 2/0805
See application file for complete search history.

(56) References Cited

U.S. PATENT DOCUMENTS

| | | |
|---|---|---|
| 5,725,541 A | 3/1998 | Anspach, III et al. |
| 5,782,865 A | 7/1998 | Grotz |
| 6,099,530 A | 8/2000 | Simonian et al. |
| 6,129,763 A | 10/2000 | Chauvin et al. |
| 2001/0051807 A1 | 12/2001 | Grafton |
| 2006/0235410 A1* | 10/2006 | Ralph ................ A61B 17/8038 606/313 |
| 2010/0262285 A1 | 10/2010 | Teranaka |
| 2012/0296427 A1* | 11/2012 | Conner ................. A61F 2/0805 623/13.13 |
| 2013/0144334 A1* | 6/2013 | Bouduban .......... A61B 17/0401 606/232 |
| 2013/0172944 A1* | 7/2013 | Fritzinger .......... A61B 17/0401 606/286 |
| 2013/0190817 A1* | 7/2013 | Bouduban ............ A61B 17/866 606/232 |

FOREIGN PATENT DOCUMENTS

| | | |
|---|---|---|
| EP | 0 611 557 | 4/1999 |
| FR | 2 753 368 | 3/1998 |
| GB | 2 084 468 | 6/1984 |
| JP | 2002511306 | 4/2002 |
| WO | 2003/071962 | 9/2003 |
| WO | 2013/071234 | 5/2013 |

\* cited by examiner

ORTHOPAEDIC BONE ANCHOR AND SUSPENSION DEVICE

This application is a National Stage entry under § 371 of International Application No. PCT/EP2017/072722, filed on Sep. 11, 2017, and which claims the benefit of German Application No. 10 2016 117 490.4, filed on Sep. 16, 2016.

The present invention relates to a simultaneous orthopaedic bone anchor and suspension device, in particular a bone anchor and suspension device which can be used especially for the treatment of injuries of the acromioclavicular joint, but also for the treatment of other bone, ligament and joint injuries, for example in tearing of the biceps tendon at the elbow joint, secondary rupture of the cruciate ligament of the knee, rupture of the syndesmosis at the ankle joint.

Accidents, in particular sports accidents, involving a violent force acting directly on the shoulder often lead to injuries of the acromioclavicular joint, the connection between the acromion and the clavicle, referred to in short as the AC joint. Mild injuries of the AC joint, such as contusions or low-grade ligament tears, can be successfully treated by non-surgical measures. By contrast, in cases of more serious injuries, this approach is often inadequate, particularly in injuries that are characterized by complete tears of the coracoclavicular ligaments, i.e. the ligaments between clavicle and coracoid (the coracoid process of the shoulder blade), or in injuries of the AC joint that involve specific bone fractures. In these cases, surgical treatment is indicated if there is the possibility of such injuries leading to permanently decreased function as a result of vertical or horizontal instabilities of the outer end of the clavicle. The degree of severity of such instabilities is classed according to Tossy or, still more precisely, with the Rockwood classification. Accordingly, injuries of type III (Tossy) or of type IIIB-IV (Rockwood) are treated surgically.

Fresh injuries of the acromioclavicular joint, i.e. when a period of less than 2 to 3 weeks has passed since the trauma, are usually reduced manually and maintained either by a plate or wires, or by means of special fastening sutures, the so-called suture tension implants.

In addition to its other possible complications, stabilization with a plate or wires has the general disadvantage that a second intervention is required at the end of the treatment in order to remove the implant. By contrast, the so-called suture tension implants or suture anchor implants can be left in place in the body. For the stabilization of the correct position of the clavicle with the aid of these suture tension implants, several continuous bore channels or holes are usually worked both into the clavicle and also into the coracoid, through which channels the fastening sutures are pulled and then, depending on the product, anchored on holding buttons or plates on the upper face of the bore channels in the clavicle and on the underside of the bore channels in the coracoid. In cases of chronic instability, the implant has to be supplemented by an tendon (for example, from the area of the knee joint, the semitendinosus tendon or the gracilis tendon) or by an artificial ligament for anatomical reconstruction, which is either placed like a loop between clavicle and coracoid or is clamped with screws in specially provided bore channels. Both procedures take up a great deal of time and are correspondingly susceptible to complications since, in the final analysis, various approaches have to be made below the coracoid in order to test the position of the anchor, to pull the grafts through and to fix them, etc.

Numerous disadvantages of these modern, flexible anchoring and suspension methods are known. The increased thickness or increased number of the bore channels can lead to bone fractures, especially at the coracoid. Subsequently, patients may be caused discomfort by fastening knots lying beneath the skin, especially on top of the clavicle. Widening of the bone tunnel is often also observed. Moreover, tendon slings are able to saw through the bone (clavicle and coracoid). The abutments (buttons, knots, etc.) can break through the bone shell, screw anchors can tear off and shift, etc.

The direct consequence of this is often the loss of the surgical result, and in many cases surgery often has to be repeated. Such follow-up operations require further bores and are therefore even more complex and accordingly more susceptible to complications.

US patent application US 2001/051807 A1 describes a bioabsorbable, cannulated expandable tissue anchor for sutureless soft tissue fixation to bone, particularly in arthroscopic shoulder surgery. The anchor is provided with a ribbed shaft and a head having several barbs at its underside for securing the soft tissue to bone. The shaft of the anchor is divided into at least two legs by longitudinal slots which extend from the distal end of the anchor. After the anchor is installed through tissue and into bone, a dowel is inserted into the proximal end of the cannulated shaft to axially spread apart the legs of the shaft by opening the longitudinal slots, thereby securing the anchor in the bone. While the tissue anchor of US 2001/051807 A1 is suitable for fixing tissue to the outside of a bone, it is unsuitable for fixing, for instance AC-instabilities where suture wire material and/or graft tissue material has to be guided through a bone channel provided in the clavicle and fixed by the bone anchor.

The same limitations are found when employing an expandable toothed bone anchor as described in U.S. Pat. No. 5,782,865.

European patent application EP 0 611 551 A1, corresponding to DE 694 00 714 T2, describes a suture anchor installation system which comprises a suture anchor assembly engaged with a suture anchor insertion tool. The suture anchor assembly features a two-piece suture anchor for insertion into a pre-drilled hole in bone and at least one suture having at least one surgical needle affixed thereto. The two-piece suture anchor comprises a setting pin slidablely engaged within an engagement member having barbed legs expandable in response to proximal movement of the setting pin. The setting pin is provided with two suture accommodating slots extending longitudinally along the sides of the pin. The suture anchor insertion tool includes a body portion and a distally extending shaft portion. An annular region on the distal end of the shaft portion engages the legs of the suture anchor engagement member. A channel in the shaft portion aligns with a channel in the body portion to accommodate the suture. Needle-retaining assemblies located on the body portion of the suture anchor insertion tool engage the surgical needle or needles attached to the suture. The suture anchor installation system of EP 0 611 551 A1 is also not suited for guiding through bone channels and fixing the graft material appropriately and simultaneously augmenting the graft, etc.

The technical problem addressed by the present invention is therefore to make available a versatile orthopaedic bone anchor and suspension device which does not have the above-described problems and which permits simpler and faster treatment, in a manner less susceptible to complications, of acute and chronic instabilities of the acromioclavicular joint, also in follow-up cases. The bone anchor and suspension device according to the invention is intended to be able to be used in different operating techniques (arthroscopic, endoscopic, mini-open or open).

This technical problem is solved by the orthopaedic bone anchor and suspension device with the features of the present Claim 1. Advantageous developments of the bone anchor and suspension device according to the invention are the subject matter of the dependent claims.

The invention accordingly relates to an orthopaedic bone anchor and suspension device with a head which, on its upper face, has an opening of a central bore for receiving a preferably substantially cylindrical expansion device, and, adjoining the underside of the head, a sleeve which is designed as an expansion dowel for anchoring the bone anchor in the bone, wherein the bone anchor and suspension device according to the invention is characterized in that the head has a collar which protrudes outwards past the sleeve. The collar of the bone anchor and suspension device according to the invention has, on its outer circumference, at least one recess.

Bone anchors which can be anchored in the bone in the manner of an expansion dowel, for example in order to anchor grafts or fastening sutures in a bone, are known from other orthopaedic applications. However, none of the known bone anchors has a head with a plate-like collar protruding outwards past the sleeve embedded in the bone and being provided with a recess on its outer circumference. The collar provided in the bone anchor and suspension device according to the invention advantageously provides an abutment against pulling in the case of a fastening suture pulling downwards through the bone. Moreover, the collar bearing on the bone serves to stabilize the bone anchor and suspension device against lateral tilting, such that the orientation of the bone anchor and suspension device is precisely established prior to the fixing by means of the expansion dowel-like sleeve. The collar can be so flat, and if appropriate rounded at the surface, that it causes no discomfort to the patient, even in cases in which it is introduced into a bone lying directly beneath the skin, for example the clavicle.

The central bore is preferably designed as a continuous bore which extends through the head and the sleeve of the bone anchor and suspension device. This passage through the bone anchor and suspension device also makes it possible, for example, for the anchor and suspension device to be guided to the bone bore channel via a guide wire, which can be applied at the outset as an aid. Subsequently, by way of this wire, a hole of suitable dimensions can be drilled exactly, and the expansion dowel, with or without graft, can be introduced with a precise fit. When introducing the orthopaedic bone anchor and suspension device according to the invention, it is therefore no longer absolutely necessary to visually monitor the procedure by endoscopy or otherwise. Moreover, there is a considerable saving in time, which is very important both from a medical and also from a financial point of view, since the risks and costs of an operation increase with the duration of the intervention.

The recesses provided on the outer circumference of the bone anchor and suspension device allow a graft, for example an auto-tendon graft or an allo-tendon graft, to be guided through this recess into the bone bore channel and anchored there, without any danger of the graft being damaged by the plate-like collar of the bone anchor and suspension device.

Depending on the particular application, the fixing of the bone anchor and suspension device by means of an expansion dowel already provides a certain abutment function, such that the collar in these cases only has to protrude slightly past the outer circumference of the sleeve. In these cases, the sutures can be fixed by the clamping function of the sleeve between the inner wall of the bone bore channel and the outer wall of the sleeve. Moreover, the expansion device can also have securing possibilities for the fastening sutures.

However, fastening sutures can also be fixed at the collar of the bone anchor and suspension device. For this purpose, according to a preferred embodiment of the orthopaedic bone anchor and suspension device, the collar has at least one hole for receiving a fastening suture, as is required for example for producing suture tension implants for stabilizing the reduced acromioclavicular joint. Several holes of this kind are preferably provided in the collar of the bone anchor and suspension device and surround the opening of the central bore. It is particularly preferable that four holes of this kind are provided in the collar for fastening sutures.

In one embodiment, in which holes for receiving fastening sutures and also recesses for grafts are provided in the collar, the anchoring of fastening sutures and the fixing of the graft can particularly advantageously be carried out in one step.

On account of the special design of the orthopaedic bone anchor and suspension device according to the invention, the bone anchor and suspension device can be introduced from above into the coracoid or clavicle in the stabilization of the acromioclavicular joint, such that a single access from above is sufficient for anchoring the fastening sutures both in the clavicle and also in the coracoid.

Moreover the device of the present invention is a "simultaneous bone anchor and suspension device" because a single design of the device can be used either as a bone anchor, especially when using the sleeve of the device as an expansion dowel, or as a suspension device. The first type of use (anchor) is preferred when an upward strain acts on the bone anchor and suspension device, e.g. when the device is inserted into a bone bore hole in the coracoid during AC instability surgery. The second type of use (suspension device) is preferred when a downward strain acts on the device, e.g. when placed in the bone channel of the clavicle during AC instability surgery. When using the device of the invention as a suspension device, it is often not necessary to employ an expansion device. Rather, the bone anchor and suspension device can be inserted into to bone channel which has an inner diameter which essentially corresponds to the outer diameter of the sleeve of the device. In these cases, an expansion of the sleeve is often not required. Rather, when a downward strain is exerted by sutures and/or graft, the head of the device having a greater diameter than the inner diameter of the bone hole will abut on the outer surface of the bone thus preventing the device from being further inserted into the bone channel.

In order to facilitate insertion of the bone anchor and suspension device into the bone channel, the circumferential edge of the underside of the sleeve can be slanted.

On account of the possible reduction to a single bone bore hole in the coracoid, which is filled by the orthopaedic bone anchor and suspension device, with the sutures being secured on the collar of the bone anchor and suspension device, there is substantially less risk of a fracture caused by tunnel widening, drilling, etc. This also applies to drilling in the clavicle, wherein the sutures are expanded between dowel and bone, knotted under the clavicle and shortened. In this way, it is possible to avoid a situation where the patient experiences irritation caused by fastening knots that can be felt under the skin.

Finally, with the bone anchor and suspension device according to the invention, it is not necessary to place a graft as a loop around the coracoid or the clavicle, and instead the graft can be placed in the bore bone channel or hole, i.e.

within the bone, in a step with the application of the fastening sutures and can be fixed between the outer wall of the sleeve and the inner wall of the bone bore channel by means of the expansion dowel-like sleeve of the bone anchor and suspension device according to the invention. Alternatively, the graft can be fixed on top of the bone between the underside of the head of the anchor and the surface of the bone. The bone anchor and suspension device according to the invention can thus be used both for stabilization of acute AC joint instabilities and also for the combined augmented biological (or non-biological) stabilization of chronic instabilities.

The bone anchor and suspension device according to the invention can be applied not only by conventional open surgical techniques but also by arthroscopic, endoscopic or mini-open surgical techniques.

With the bone anchor and suspension device according to the invention, it is possible to minimize complications. However, even in rare cases of complications, the bone anchor can be easily removed again from the bone bore channel, when the cylindrical expansion device is first of all removed from the central bore. Furthermore, the original bone bore channel can be used again, such that in most cases there is no need to form a further bore.

In another embodiment of the invention, on its underside the head is provided with a ledge arranged between the underside of the head and the adjoining sleeve. The diameter of the ledge, measured perpendicularly to the longitudinal axis of the central bore, is smaller than the diameter of the head so that the ledge provides a step-like junction between the underside of the head and the sleeve of the bone anchor and suspension device.

In a further embodiment, the internal diameter of the sleeve narrows towards its lower end, such that the sleeve increases its outer circumference upon introduction of the cylindrical expansion device.

The lower end of the sleeve, or the sleeve as a whole, can have a conical overall shape. For example, depending on the required dimensions, the sleeve, directly after the head thereof, can have a cylindrical neck which has a substantially constant diameter and which is adjoined by a conical end portion, where the external diameter of the sleeve narrows towards its lower end.

Where lower end and upper end are mentioned in the present context, lower end signifies the end of the bone anchor and suspension device directed into the bore channel worked into the bone, whereas the upper end of the head with the collar of the bone anchor and suspension device bears on the bore channel.

In the area of the collar and/or in the area of the sleeve, the central bore of the bone anchor and suspension device preferably has an inner thread into which the cylindrical expansion device can be screwed. In this case, the cylindrical expansion device is particularly preferably designed as a screw, which is screwed, if appropriate reversibly, into the collar or the sleeve.

At its lower end, the sleeve particularly preferably has at least two longitudinal slits, which define at least two wings of the sleeve. When the cylindrical expansion device is introduced, for example screwed in, these wings are forced outwards and thus clamp the bone anchor and suspension device securely in the bone bore channel. According to a particularly preferred embodiment, four longitudinal slits are provided in the sleeve, such that the lower end of the sleeve has four wings. In this variant, the forces acting on the bore channel as a result of the introduction of the expansion device are distributed more uniformly.

In a preferred embodiment, the outer surface of the sleeve is smooth, i.e. even and unruffled, thus allowing for an easy removal or replacement of the bone anchor and suspension device of the invention, e.g. in case of a revision surgery. Especially in the case of a smooth outer surface, it is advantageous if the neighboring slits provided in the sleeve have different lengths. In this embodiment, introducing the expansion device will result in a tilted outward movement of the wings allowing the bone anchor and suspension device to be more securely jammed within the bone channel. In addition, the tilted wings prevent a rotation of the bone anchor and suspension device during insertion of the expansion device. Alternatively or in addition, the wings may also have different lengths.

The bone anchor and suspension device is advantageously made of a biocompatible material, in particular a biocompatible metal or a biocompatible metal alloy, a biocompatible plastic or a biocompatible composite. The bone anchor and suspension device is particularly preferably made of plastic, in particular of polyether ether ketone (PEEK). Accordingly, the bone anchor and suspension device made from a biocompatible plastic material will therefore present no danger in magnetic resonance diagnostic or imaging procedures. Furthermore, using a non-absorbable material facilitates extraction of the anchor in case of revision.

Typical dimensions of the bone anchor and suspension device according to the invention, when used for treatment of the acromioclavicular joint, lie within the range of millimeters. Thus, the length of the sleeve is typically 4 to 15 mm, preferably 4-10 mm, and its external diameter 3 to 6 mm. The height of the collar is usually 1-2 mm, and the external diameter typically 4 to 8 mm. The invention also relates to an orthopaedic fixing system, which comprises a bone anchor and suspension device as defined above and an expansion device.

According to a variant of the invention, the expansion device can have means for the securing of fastening sutures, such that a bone anchor and suspension device does not necessarily have to be used that has holes in the collar for corresponding fastening sutures.

The expansion device can be designed like a nail, for example, and hammered into the central bore of the bone anchor and suspension device. However, the expansion device is particularly preferably a screw, in particular a grub screw, i.e. a threaded pin without a pronounced screw head, or a cortical screw, each of which facilitates easy removal of the bone anchor and suspension device from the bone. A grub screw is particularly preferred when no part of the screw is intended to protrude above the upper face of the head of the bone anchor and suspension device, which is in particular the case when the bone anchor and suspension device according to the invention is anchored on the upper face of the clavicle. In other variants, the screw can be a cortical screw or a cancellous screw, for example when the bone anchor and suspension device is anchored in the coracoid, which has the additional advantage that the bone anchor and suspension device is fixed at the lower end in the opposite cortical layer not only on account of the clamping function in the manner of an expansion dowel but also by means of the cortical screw, in order to obtain a still greater resistance to pulling out. As a further option, it is also conceivable to combine the bone anchor and suspension device according to the invention with conventional screw anchors as expansion element, which would permit a still wider range of use.

The fixing system according to the invention can moreover comprise a guide wire, which permits the formation of the bore holes and the application of the bone anchor and suspension device without direct sighting.

The expansion device of the fixing system according to the invention is preferably made of titanium or PEEK and can be solid or hollowed (cannulated). Typical screws serving as an expansion device have a diameter of 2.7 mm to 3.5 mm, although this is to be regarded as variable in respect of extended indications and in relation to the overall size of the respective implant. An anchor at the wrist, for example, is much smaller than an anchor at the knee joint, since the latter anchor would have to be made stronger on account of the greater forces that have to be taken up. Grub screws are typically up to 15 mm long but should not extend beyond the device of the invention, whereas cortical screws are usually longer, depending on the individual size.

The fastening sutures used are preferably made of ultra-strong suturing material of variable diameters, for example FiberWire® from Arthrex, which is a suture with a multi-stranded core of ultra-high molecular weight polyethylene (UHMWPE) with a braided sleeve of polyester and UHMWPE. In AC surgery, suture diameters up to #5 (USP designation) or even thicker can be used with the bone anchor and suspension device of the invention.

The invention is explained in more detail below on the basis of an illustrative embodiment shown in the accompanying drawings, in which.

Figure 1:
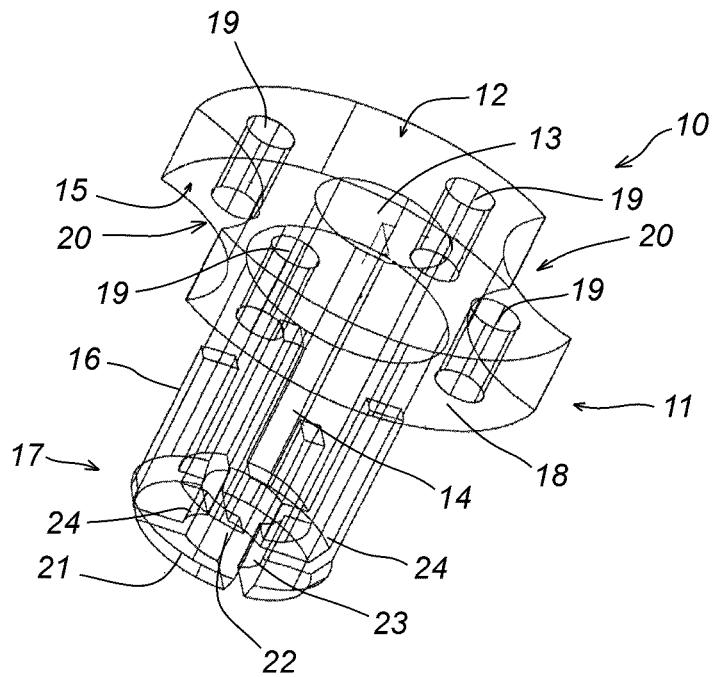
FIG. 1 shows a perspective transparent plan view of an embodiment of the orthopaedic bone anchor and suspension device according to the invention.

In FIG. 1, a first embodiment of the orthopaedic bone anchor and suspension device according to the invention is designated overall by the reference number 10. In the following, for the sake of conciseness, the bone anchor and suspension device of the invention will be simply be referred to as "bone anchor".

The bone anchor 10 has a head 11, on the upper face 12 of which an opening 13 of a central bore 14 is discernible which extends along the longitudinal axis of the bone anchor 10. The underside 15 of the head 11 is adjoined by a sleeve 16 which is designed as an expansion dowel for subsequently anchoring the bone anchor in the bone and for fixing a graft or fastening sutures between sleeve and bone bore. For this purpose, an expansion device (not shown in FIG. 1) is inserted into the bore 14 via the opening 13 and widens the sleeve 16 out, at least at the underside 17 thereof, and thereby anchors the bone anchor in a bore channel or hole that has been excavated in the bone. The head 11 moreover has a plate-like collar 18 which protrudes outward past the sleeve 16, i.e. at least at some locations on its circumference has an external diameter greater than the external diameter of the sleeve 16. The underside 15 of the collar 18 of the head 11 protruding past the sleeve thus forms a bearing surface, with which the orthopaedic bone anchor can bear on the bone surface surrounding the bore channel of the bone. In the collar 18 protruding outwards past the sleeve 16, holes 19 are formed at which fastening sutures can be arranged for the subsequent stabilizing of a bone such as the clavicle and the graft can be secured to the anchor. Moreover, the outer circumference of the collar 18 is provided with two concave recesses 20 which lie opposite each other and in the region of which the external diameter of the collar decreases but is still at least as great as the external diameter of the sleeve 16. The recesses 20 facilitate the subsequent passage of a graft, for example a tendon, which is then guided into the bone bore channel and can be fixed by means of the sleeve 16 acting as an expansion dowel or is just threaded and secured to the anchor to be fixed on the bone surface. In the embodiment shown, the central bore 14 passes all the way through the bone anchor. In other words, in addition to the upper opening 13 on the upper face 12 of the head 11, the bore 14 also forms a lower opening 22 on the underside 21 of the sleeve 16. The internal diameter of the bore 14 narrows from its upper end to its lower end. In other words, in the example shown, the diameter of the upper opening 13 is greater than the diameter of the lower opening 22. Upon the insertion of an expansion device, the outer circumference of the sleeve 16 thus increases in size the farther the expansion device is introduced into the bore 14. At its lower end 17, the sleeve 16 itself also narrows conically, i.e. its external diameter decreases.

A screw is often used as the expansion device and can be screwed into the bore 14. If the screw is made of a harder material than the bone anchor, a self-tapping screw can be used which, as it is screwed in, cuts a corresponding thread into the inner face of the bore 14. In the area of the collar 18 and/or of the sleeve 16, the bore preferably has a previously introduced thread, which makes it easier to screw in the expansion device. For the sake of clarity, this inner thread is not illustrated in the example shown.

In the depicted embodiment of the bone anchor, four longitudinal slits 23 are formed in the area of the lower end 17 of the sleeve 16, and they divide the lower end 17 of the sleeve 16 into four wings 24 which, upon insertion of the expansion device into the bore 14, are able to fold outward (expansion wings) and thereby ensure the necessary anchoring of the bone anchor in the bone bore channel.

Figure 2:
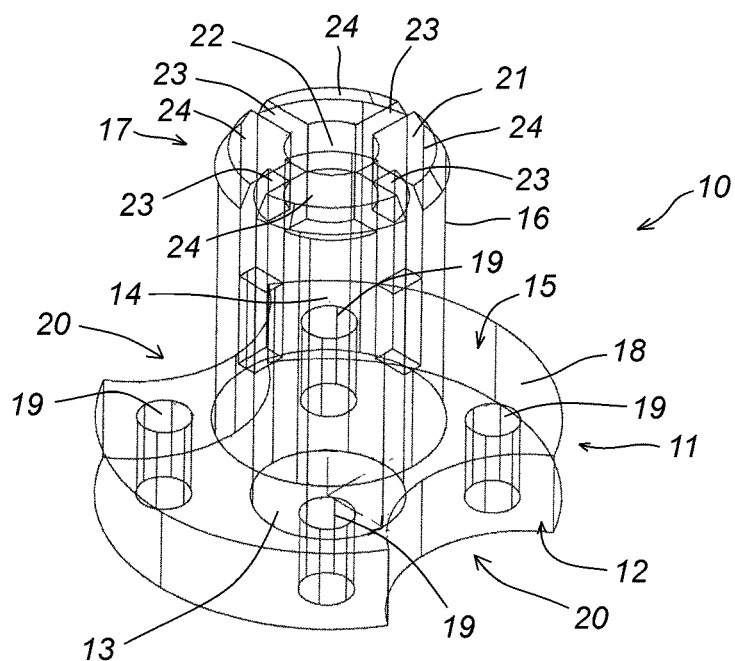
FIG. 2 shows a perspective transparent bottom view of the bone anchor and suspension device from FIG. 1.

FIG. 2 shows the bone anchor 10 from FIG. 1 in another perspective view, with the same reference numbers being used to designate the same elements.

Figure 3:
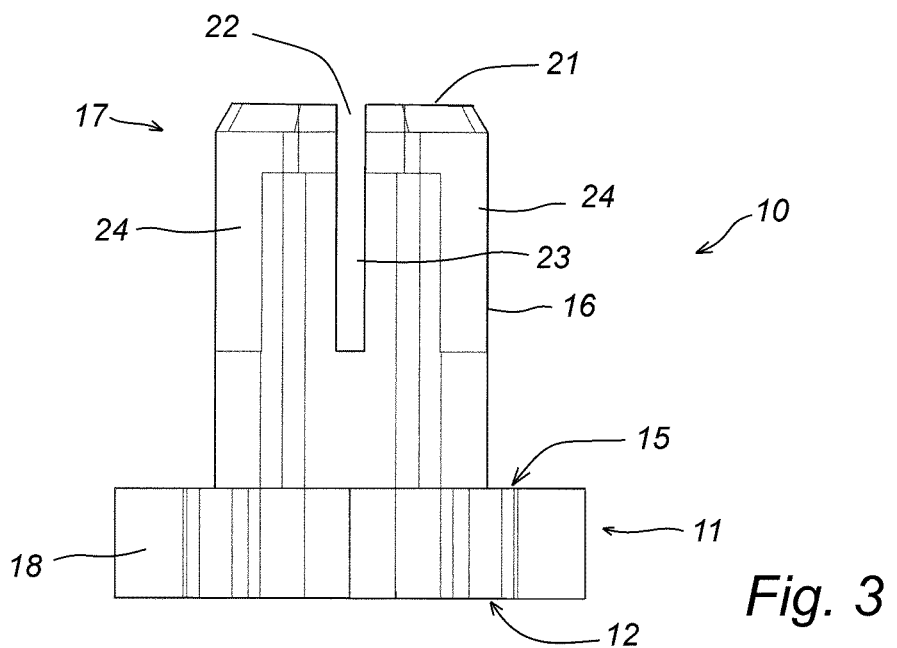
FIG. 3 shows a non-transparent side view of the bone anchor and suspension device from FIGS. 1 and 2.

The side view in FIG. 3 shows in particular a longitudinal slit 23 and two of the wings 24 especially clearly. Here too, the same reference numbers are again used as in FIGS. 1 and 2.

Figure 4:
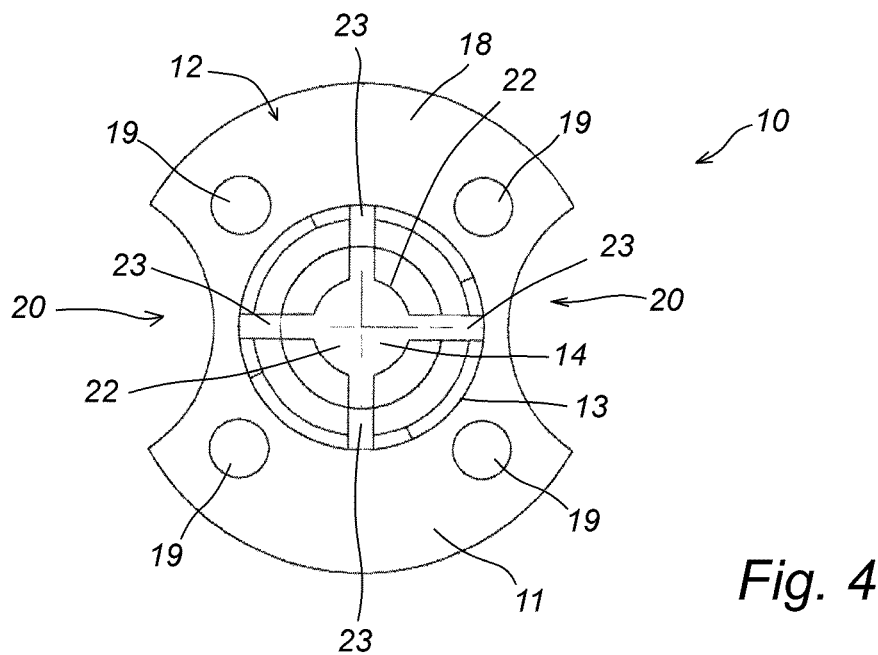
FIG. 4 shows a non-transparent plan view of the bone anchor and suspension device from FIGS. 1-3.

The same reference numbers as in FIGS. 1-3 are used once again in the plan view in FIG. 4. The latter shows in particular that the upper opening 13 has a greater diameter than the lower opening 22.

Figures 5, 6:
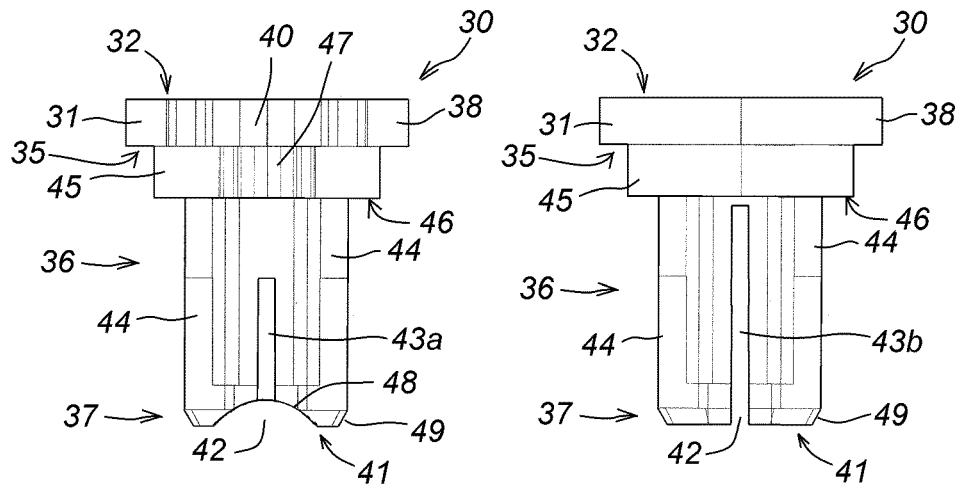
FIG. 5 shows a side view of a variant of the bone anchor and suspension device of FIGS. 1 to 4.
FIG. 6 shows another side view of the bone anchor and suspension device of FIG. 5 rotated by 90 degrees.

FIGS. 5 and 6 show side views of a variant of the bone anchor of FIGS. 1 to 4, with the view of FIG. 6 being rotated by 90 degrees with respect to the view of FIG. 5. Features of the bone anchor of FIGS. 5 and 6 which correspond to features of the bone anchor of FIGS. 1 to 4 or which perform similar functions are denoted be the same reference numbers increased by 20 and are not described in detail again.

Accordingly, the second embodiment of the orthopaedic bone anchor and suspension device according to the invention is designated overall by the reference number 30. The bone anchor 30 has a head 31, on the upper face 32 of which an opening of a central bore (the opening and the bore are not visible in the views of FIGS. 5 and 6. The underside 35 of the head 31, a ledge 45 is provided and the underside of the ledge 46 is adjoined by a sleeve 36 which is also designed as an expansion dowel for subsequently anchoring the bone anchor in the bone and for fixing a graft or fastening sutures between sleeve and bone bore. The diameter of the ledge 45 is smaller than the diameter of the head 31 so that the collar 38 of head 1 extends laterally beyond the ledge 45. Thus, depending on the width of the bone bore channel or hole into which the bone anchor 30 is inserted, it can either rest with the underside 46 of the ledge 45 on the outer surface of a bone, or with the underside 35 of the collar 38 of head 31. In the first case, the step-like gap provided beneath the underside 35 of collar 38 and the outer surface of the bone allows, for instance, graft being guided around the bone anchor without risk of damaging the graft material.

As can be taken from FIGS. 5 and 6, neighboring slits 43a, 43b provided in the sleeve have different lengths resulting in a tilted outward movement of the wings 44 upon insertion of an expansion device for more securely jamming the bone anchor within the bone bore channel.

Similar to the bone anchor of FIGS. 1-4, the head 31 of the bone anchor of FIGS. 5 and 6 is provided with recesses 40 on its circumference. Similarly, the circumference of the ledge 45 can be provided with suitably aligned recesses 47. In the embodiment depicted in FIGS. 5 and 6, the underside 41 of sleeve 36 is further provided with a groove 48. Accordingly, a graft material can be guided downward through recesses 40, 47, passed to the opposite site of the bone anchor vie groove 48 and upward through different recesses 40, 47 provided on the opposite side of the bone anchor.

Figure 7:
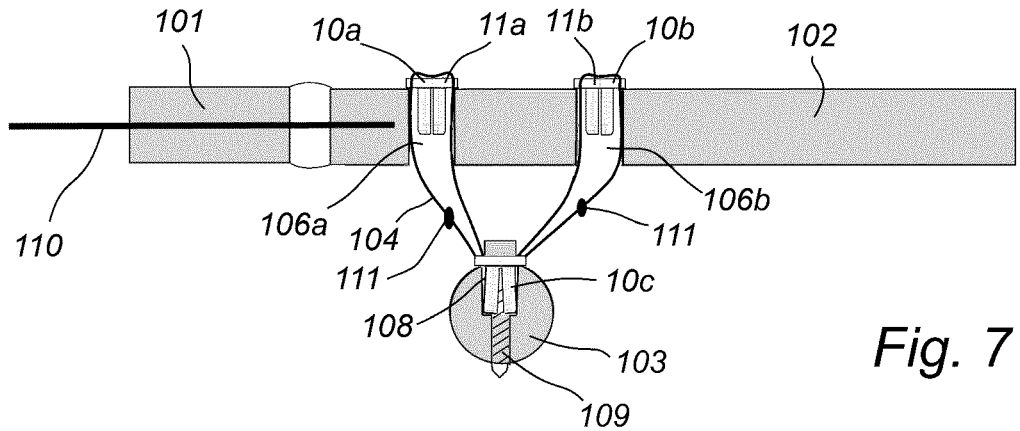
FIG. 7 shows a schematic view of the stabilizing of an acute acromioclavicular joint instability with the aid of the bone anchor and suspension device of FIGS. 1 to 4.

FIG. 7 is a schematic view showing the use of the bone anchor as depicted in FIGS. 1 to 4 for stabilizing an acute instability of an acromioclavicular joint 100, which connects the acromion 101 to the clavicle 102. Following a rupture of the ligaments between clavicle 102 and coracoid 103, intermittent stabilization of acromion and clavicle can be accomplished by means of a transarticular Kirschner wire (K-wire) 110. Afterwards suture fixation is effected, for example, by means of a bone bore hole 108, which does not necessarily have to be continuous, which is drilled into the coracoid 103. A bone anchor 10c is inserted from above into this bore. The depth of the bore hole 108 corresponds approximately to the sleeve length, that is to say approximately 6 mm. Similarly, continuous bone bore channels 106a, 106b are drilled into the clavicle 102. Fastening sutures 104 are anchored on the bone anchor 10c and are guided through the bores 106a, 106b in the clavicle to the heads of bone anchors 10a, 10b, respectively which are inserted from above into the bore channels 106a, 106b of the clavicle 102. The fastening sutures 104 are guided over the head of anchors 10a, 10b, respectively, and guided downwards through channels 106a, 106b again on opposite sides of anchors 10a, 10b. Finally, the fastening sutures are adapted in length such that the clavicle is fixed at the correct site and its ends a knotted together with knot 111. As can also be taken from FIG. 7, due to the design of the bone anchor and suspension device of the present invention, the knot (or knots) required to tie the fixing sutures or graft material together can be arranged under the clavicle and do therefore not irritate the skin of the patient at the shoulder region. In the example, the heads 11a, 11b of bone anchors 10a, 10b rest on the upper surface of the clavicle 102 so that the downward strain exerted by fastening sutures 104 on anchors 10a, 10b is sufficient to hold the anchors in place. Thus, in this embodiment, an expansion is not required for bone anchors 10a, 10b. However, an upward strain is exerted on bone anchor 10c. Therefore, an expansion device is used to expand bone anchor 10c to fix it in the coracoid 103. The bone anchor 10c can even be fixed more securely, if a cortical screw 109 is used as an expansion device. As depicted in FIG. 7, the cortical screw 109 extends beyond the bottom of bore hole 108 into the bulk coracoid.

Figure 8:
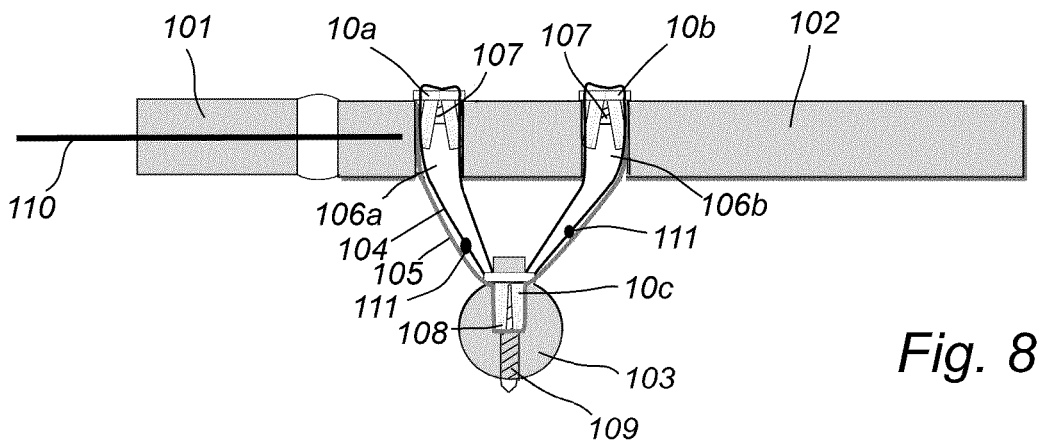
FIG. 8 shows a schematic view of the stabilizing of a chronic acromioclavicular joint instability with the aid of the bone anchor and suspension device of FIGS. 1 to 4.

FIG. 8 shows a schematic view of a stabilizing of a chronic acromioclavicular joint instability. The procedure essentially corresponds to the procedure of FIG. 7. In addition to the fixing by sutures 104, in this case further stabilization has been effected via a likewise schematically depicted graft 105, for example an auto- or allo-tendon, which grafts are fixed in the bone bores by means of the bone anchors 10a, 10b, 10c which have been introduced into the clavicle 102 and the coracoid 103, respectively. In the present example, grub screws, schematically denoted by reference sign 107, are used to expand bone anchors 10a, 10b, while a cortical screw 109 is used to expand bone anchor 10c.

As can be seen in the examples of FIGS. 7 and 8, the same bone anchor can be used in the clavicle 102 (i.e. bone anchors 10a, 10b) where strain exerted by sutures 104 and/or graft 105 acts downwardly, or in the coracoid 103 (bone anchor 10c) with strain acting upwardly.

Figure 9:
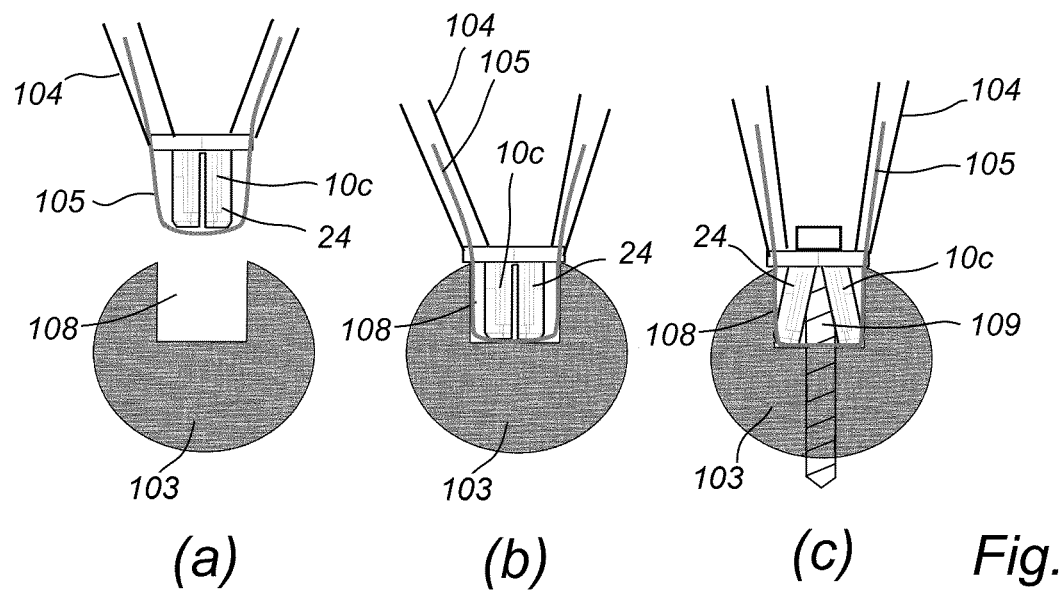
FIG. 9 shows a schematic view of the anchoring of the bone anchor and suspension device according to the invention in the coracoid.

In FIG. 9, the introduction and fixing of the bone anchor 10c according to the invention in the coracoid 103 is shown schematically in three steps. First, in step (a), a non-continuous bone bore hole 108 is worked into the coracoid 103. Then, in step (b), the bone anchor 10c is introduced into the bone bore hole 108 together with the fastening sutures 104 secured on its head and with a tendon 105 serving as graft. In step (c), a cortical screw 109 is screwed into the bone anchor 10c, such that the wings 24 of the latter are spread outwards and fix the bone anchor in the bone bore hole 108. In the example shown, the cortical screw 109 is longer than the sleeve of the bone anchor and therefore protrudes with its lower end 108 into the coracoid and out of the opposite cortical layer. The bone anchor 10c is thus fixed two-fold by the expansion wings 24 and also by the cortical screw 109.

Figure 10:
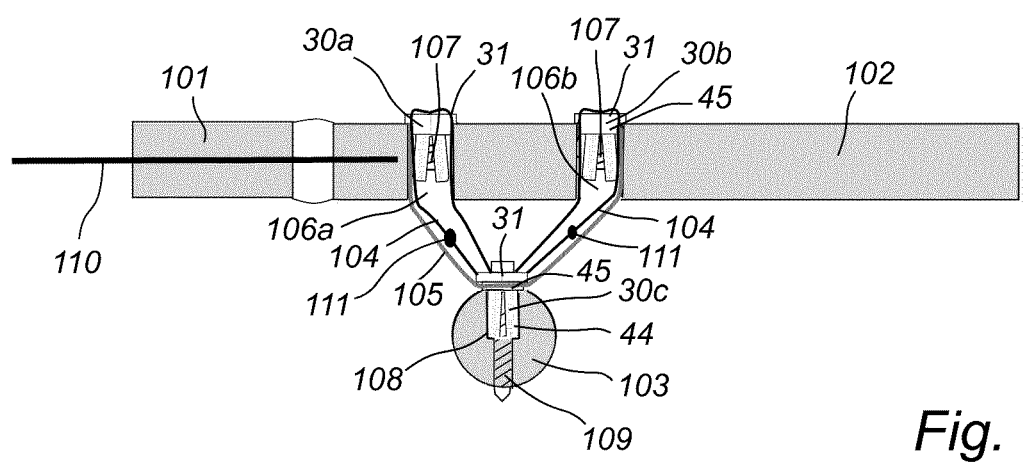
FIG. 10 shows a similar view as FIG. 7 using the bone anchor and suspension device of FIGS. 5 and 6.

FIG. 10 shows a similar view as FIG. 8 but using the bone anchor 30 of FIGS. 5 and 6. As can be taken from the depicted embodiment, bone anchors 30a, 30b are inserted in bone channels 106 provided in clavicle 102 which have an inner diameter which is larger than the outer diameter of ledge 45 but smaller than the outer diameter of the head 31. Consequently, the ledge 45 of bone anchors 30a, 30b is inserted into the bone channel 106. In contrast, the inner diameter of bone bore hole 108 provided in the coracoid 103 is smaller than the outer diameter of ledge 45 so the ledge 45 rests on the outer surface of the coracoid. In the present example, tendon 105 is not inserted into bone bore hole 108 but fixed between the underside of head 31 and the outer surface of coracoid 103.

LIST OF REFERENCE SIGNS 10,10a,10b 1$^{st}$ bone anchor and suspension device
11, 11a, 11b head 12 upper face of the head
13 upper opening
14 bore
15 underside of the head
16 sleeve
17 lower end of the sleeve
18 collar
19 hole
20 recess
21 underside of the sleeve
22 lower opening
23 longitudinal slit
24 wing of the sleeve
30,30a,30b,30c $2^{nd}$ bone anchor and suspension device
31 head
32 upper face of the head
35 underside of the head
36 sleeve
37 lower end of the sleeve
38 collar
40 recess in head
41 underside of the sleeve
42 lower opening
43a, 43b longitudinal slits
44 wing of the sleeve
45 ledge
46 underside of ledge
47 recess in ledge
48 groove in underside of sleeve
49 slanted edge
100 acromioclavicular joint
101 shoulder level/acromion
102 clavicle
103 coracoid process
104 fastening suture
105 graft/tendon
106a, 106b bone channel in clavicle
107 expansion device (grub screw)
108 bone bore hole in coracoid
109 expansion device (cortical screw)
110 transarticular Kirschner wire (K-wire)
111 knot

The invention claimed is:

1. A single-piece device that can be used as an orthopaedic bone anchor or suspension device, comprising:
a head which has an upper face, and on the upper face, has an opening of a central bore for receiving an expansion device and,
a sleeve which is designed as an expansion dowel for anchoring the device in a bone, the sleeve adjoining an underside of the head,
wherein the head has a collar which protrudes outwards past the sleeve, the collar has an outer circumference having, on the outer circumference, at least one concave recess extending from an upper face of the head to an underside of the head and arranged to allow passage of a graft without damage of the graft, and wherein the at least one concave recess consists of only two concave recesses,
the collar being further provided with at least one cylindrical hole for receiving a fastening suture,
wherein the bore has an inner thread in the area of the collar and/or in the area of the sleeve, and
wherein the sleeve has an outer surface, and the outer surface is smooth.

2. The device according to claim 1, wherein, on the underside of the head, the head comprises a ledge arranged between the underside of the head and the adjoining sleeve.

3. The device according to claim 2, wherein an underside of the sleeve is provided with a groove.

4. The device according to claim 1, wherein the central bore extends through the sleeve providing an internal diameter of the sleeve, wherein at least the internal diameter of the sleeve narrows towards a lower end thereof.

5. The device according to claim 1, wherein a lower end of the sleeve has a conical overall shape.

6. The device according to claim 1, wherein the sleeve has, at a lower end, at least two longitudinal slits which define at least two wings of the sleeve.

7. The device according to claim 1, wherein the bone anchor and suspension device is made of a biocompatible material.

8. The device according to claim 1, wherein the bone anchor and suspension device is made of polyether ether ketone (PEEK).

9. A system comprising a device according to claim 1, and a fastening suture passing through the at least one cylindrical hole.

10. The device according to claim 1, wherein the two concave recesses lie opposite each other.

11. The device according to claim 10, wherein the at least one cylindrical hole comprises at least two cylindrical holes.

12. The device according to claim 11, wherein between the two concave recesses are located two of the at least two cylindrical holes.

13. The device according to claim 10, wherein the at least one cylindrical hole comprises four cylindrical holes.

14. The device according to claim 13, wherein the four cylindrical holes are arranged such that two of the cylindrical holes are located opposite the other two cylindrical holes.

15. A system, comprising:
a device according to claim 1, and
a graft passing through one or both of the only two concave recesses.

16. A system according to claim 15, further comprising a fastening suture passing through the at least one cylindrical hole.

17. An orthopaedic fixing system, which comprises:
a device according to claim 1 and an expansion device, wherein the expansion device is a grub screw or a cortical screw.

18. The fixing system according to claim 17, wherein the expansion device is adapted to secure fastening sutures.

19. The fixing system according to claim 17, further comprising a guide wire.

20. The device according to claim 1, wherein the device is made of a biocompatible metal or a metal alloy, a biocompatible plastic, or a biocompatible composite.

* * * * *